United States Patent [19]

Witzel

[11] Patent Number: 4,782,080
[45] Date of Patent: Nov. 1, 1988

[54] N-ALKENYL-2-HYDROXYBENZO(B)THIO-PHENE-3-CARBOXAMIDE DERIVATIVES AS DUAL CYCLOOXYGENASE AND LIPOXYGENASE INHIBITORS

[75] Inventor: Bruce E. Witzel, Westfield, N.J.
[73] Assignee: Merck & Co., Inc., Rahway, N.J.
[21] Appl. No.: 776,535
[22] Filed: Sep. 16, 1985
[51] Int. Cl.$^4$ .................... A61K 31/38; C07D 333/66
[52] U.S. Cl. ........................................ 814/443; 549/55
[58] Field of Search .................... 549/55, 53; 514/443

[56] References Cited

U.S. PATENT DOCUMENTS

| | | |
|---|---|---|
| 3,413,308 | 11/1968 | Bockstahler . |
| 3,862,320 | 1/1975 | Thominet . |
| 3,907,826 | 9/1975 | Stoss et al. . |
| 3,954,748 | 5/1976 | Thominet . |
| 4,260,779 | 4/1981 | Bernasconi et al. .................. 549/55 |
| 4,396,621 | 8/1983 | Bernasconi . |

*Primary Examiner*—Alan Siegel
*Attorney, Agent, or Firm*—Theresa Y. Cheng; Michael C. Sudol

[57] ABSTRACT

N-Alkenyl-2-hydroxybenzo[b]thiophene-3-carboxamide derivatives are prepared via treatment of the corresponding unsubstituted carboxamide with appropriate agents, such as aldehydes, ketones, enol ethers, epoxides, acetals or ketals.

These compounds have been found to be effective inhibitors of both cyclooxygenase and lipoxygenase and thereby useful in the treatment of pain, fever, inflammation, arthritic conditions, asthma, allergic disorders, skin diseases, cardiovascular disorders, psoriasis, inflammatory bowel disease, glaucoma or other prostaglandins and/or leukotriene mediated diseases.

6 Claims, No Drawings

N-ALKENYL-2-HYDROXYBENZO(B)THIO-PHENE-3-CARBOXAMIDE DERIVATIVES AS DUAL CYCLOOXYGENASE AND LIPOXYGENASE INHIBITORS

BACKGROUND OF THE INVENTION

This invention relates to benzothiophenes, particularly 2-hydroxybenzothiophenes having the unusual 3-enamido side chains, for example,

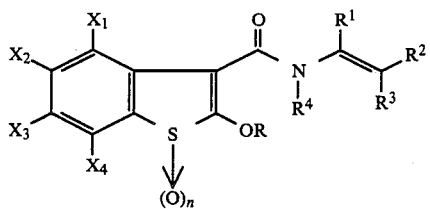

These novel compounds can be effective cyclooxygenase and 5-lipoxygenase inhibitors and therefore can be useful in the treatment of inflammation and other prostaglandins and/or leukotriene mediated diseases.

Among various potent biological mediators derived from the oxygenation of arachidonic acid, prostaglandins and leukotrienes have been linked to various diseases. Notably, the biosynthesis of prostaglandins has been identified as a cause of inflammation, arthritic conditions (e.g., rheumatoid arthritis, osteoarthritis and gout), psoriasis, inflammatory bowel disease, and pain. Furthermore, the formation of leukotrienes has been connected to immediate hypersensitivity reactions and proinflammatory effects. It has been established that arachidonic acid undergoes oxygenation via two major enzymatic pathways:

(1) The pathway catalyzed by the enzyme cyclooxygenase; and
(2) The pathway catalyzed by the enzyme 5-lipoxygenase.

Interruption of these pathways by enzyme inhibition has been explored for effective therapy. For example, non-steroidal anti-inflammatory drugs (NSAID) such as aspirin, indomethacin and diflunisal are known cyclooxygenase inhibitors which inhibit the process wherein arachidonic acid is oxygenated via cyclooxygenase to prostaglandins and thromboxanes.

Recently, it has been observed that certain leukotrienes are responsible for diseases related to immediate hypersensitivity reactions such as human asthma, allergic disorders, and skin diseases. In addition, certain leukotrienes and derivatives thereof are believed to play an important role in causing inflammation (B. Samuelsson, Science, 220, 568 (1983); D. Bailey et al. Ann. Rpts. Med. Chem., 17, 203 (1982)).

Through recent research, 5-lipoxygenase inhibitors has been linked to the treatment of eye inflammation and used as cytoprotective agents.

To be an effective and acceptable topical agent for treating eye inflammation, a drug must not only penetrate the ophthalmic tissues to reach the active sites within the eye, but it must also be devoid of those side effects including irritation, allergic reaction and the like which would militate against long term administration.

With respect to the cytoprotective activity, it has been known that (1) gastric cytoprotection does not involve inhibition of gastric acid secretion. For example, protaglandin F2B does not inhibit gastric acid secretion, but it does induce gastric cytoprotection (S. Szabo et al., Experimentia, 38, 254, 1982); (2) lower effective dosages of cytoprotective agents are required than that of gastric acid inhibitors; and (3) the cytoprotective activity of a compound may be observed in both animals and man by noting the increased resistance of gastrointestinal mucosa to strong irritants. For example, animal studies have shown that cytoprotective compounds will prevent gastric lesions induced by oral administration of strong acids, strong bases, ethanol, hypertonic saline, etc.

DETAILED DESCRIPTION OF THE INVENTION

A. Scope of the Invention

The present invention relates to novel compounds of formula (I):

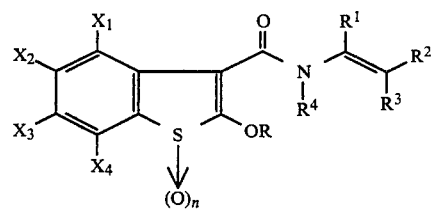

or a pharmaceutically acceptable salt thereof wherein R is
(a) H;
(b) loweralkyl, especially $C_{1-6}$ alkyl such as methyl, ethyl, i-propyl, n-propyl, t-butyl, n-butyl, i-pentyl, n-pentyl and n-hexyl;
(c) aryl especially $C_{6-14}$ aryl e.g., naphthyl, anthryl, phenyl or substituted phenyl of formula

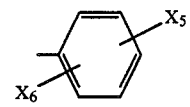

wherein $X_5$ and $X_6$ independently are:
(1) Q, where Q is H, loweralkyl especially $C_{1-6}$ alkyl, haloloweralkyl especially fluoro or chloro $C_{1-6}$ alkyl such as trifluoromethyl, phenyl or substituted phenyl, or naphthyl;
(2) halo especially chloro, fluoro, bromo or iodo;
(3) loweralkenyl especially $C_{2-6}$ alkenyl such as ethenyl and allyl;
(4) loweralkynyl especially $C_{2-6}$ alkynyl, for example, ethynyl or n-butynyl;
(5) —SQ;
(6) —OQ;
(7) —CHQCOQ$^1$, where Q is Q$^1$ and can be the same as or different from Q$^1$;
(8) —CHQCOOQ$^1$;
(10) —CH$_2$SQ or —CHQSQ$^1$;
(11) —CH$_2$OQ or —CHQOQ$^1$;
(12) —COQ;
(13) —COOQ;
(14) —OCOQ;
(15) —NQQ$^1$;
(16) —NQCOQ$^1$;
(17) —NQ(OQ$^1$);
(18) —NQ(SQ$^1$);
(19) —NQSO$_2$Q$^1$;

(20) —SO$_2$NQQ$^1$;
(21) —SOQ;
(22) —SO$_2$Q;
(23) —SO$_3$Q;
(24) —CN;
(25) —NO$_2$;
(26) —CONQQ$^1$;
(27) —NO;
(28) —CSQ;
(29) —CSNQQ$^1$;
(30) —CF$_2$SQ;
(31) —CF$_2$OQ;
(32) —NQCONHQ$^1$ or NQCONQ$^1$Q$^2$ wherein Q$^2$ is Q$^1$ and can be the same as or different from either Q or Q$^1$;

(d) lowercycloalkyl especially C$_{3-6}$ cycloalkyl, e.g., cyclopropyl, cyclopentyl and cyclohexyl;

(e) haloloweralkyl especially halo C$_{1-6}$ alkyl, e.g. CF$_3$—, CHF$_2$—, C$_2$F$_5$—;

(f) heteroaryl or heteroaryl substituted with X$_5$ and X$_6$ especially pyridyl, pyrryl, furyl or thienyl wherein X$_5$ and X$_6$ are as previously defined;

(g) benzyl or substituted benzyl of formula

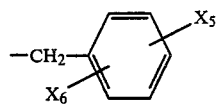

wherein X$_5$ and X$_6$ are as previously defined;

(h) loweralkynyl especially C$_{1-6}$ alkynyl such as —C≡CH; CH$_3$—C≡C—, or HC≡C—CH$_2$—;

(i) loweralkenyl especially C$_{1-6}$ alkenyl, such as CH$_2$=CH—, CH$_3$CH=CH—, CH$_2$=CHCH$_2$—, CH$_3$CH=CH—CH$_2$— or (CH$_3$)$_2$C=CH;

(j) phenylloweralkenyl of formula

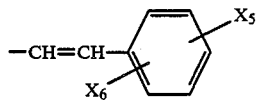

where X$_5$ and X$_6$ are as previously defined; or (k) phenylloweralkynyl of formula

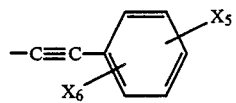

where X$_5$ and X$_6$ are as previously defined;

(l) 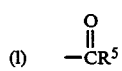

wherein R$^5$ is R;

(m) 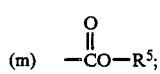

(n) 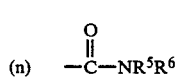

wherein R$^6$ is R$^5$ and can be the same as or different from R$^5$;

(o) 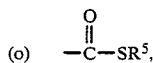

(p) 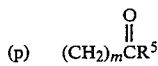

wherein m is 1 or 2;

(q) 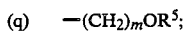

(r) 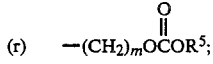

(s) 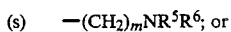

(t) 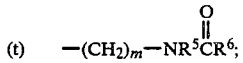

n is 0, 1 or 2;
X$_1$, X$_2$, X$_3$ and X$_4$ independently are
(a) R as previously defined; or
(b) X$_5$;
R$^1$, R$^2$ and R$^3$ independently are
(a) R; or
(b) R$^2$ and R$^3$ joined together forming a ring of structure

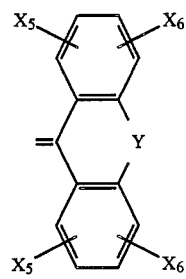

wherein X$_5$ and X$_6$ are as previously defined and Y is (CH$_2$)$_n$, O, S, SO, SO$_2$, NQ; or
(c) halo;
R$^4$ is
(a) R; or
(b) —CR$^1$=CR$^2$R$^3$;

Preferably, a dual enzyme inhibitor of this invention is of formula:

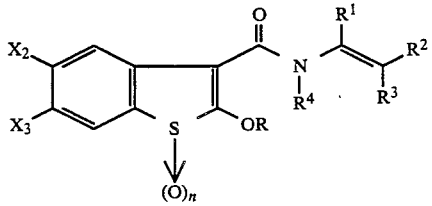

wherein X$_2$, X$_3$, R, R$^1$, R$^2$, R$^3$, R$^4$ and n are as previously defined.

More preferably, a dual enzyme inhibitor of this invention is of formula:

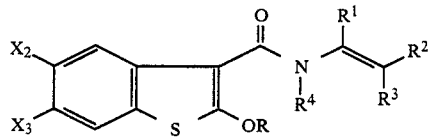

wherein $X_2$, $X_3$, R, $R^1$, $R^2$, $R^3$ and $R^4$ are as previously defined.

Even more preferably, a dual enzyme inhibitor of this invention is of formula:

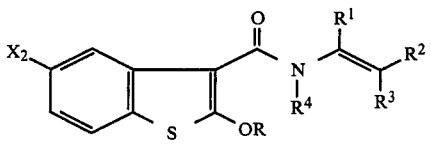

wherein
$X_2$ is
  (a) H;
  (b) loweralkyl;
  (c) haloloweralkyl especially halo-$C_{1-6}$alkyl such as $CF_3$;
  (d) loweralkenyl especially $C_{2-6}$alkenyl; or
  (e) halo;
R is H or $C_{1-6}$alkanoyl;
$R^2$ and $R^3$ independently are:
  (a) loweralkyl;
  (b) phenyl or substituted phenyl;
  (c) heteroaryl or substituted heteroaryl especially thienyl, furyl or pyrryl; and
$R^4$ is H or $-CH=CHR^2$.

The following are some representative compounds of the present invention:

N-(2,2-diphenylethenyl)-2-hydroxybenzo[b]thiophene-3-carboxamide;

N-(2,2-diphenylethenyl)-2-hydroxy-5-(trifluoromethyl)benzo[b]thiophene-3-carboxamide;

N-(2,2-diphenylethenyl)-2-hydroxy-6-(trifluoromethyl)benzo[b]thiophene-3-carboxamide;

N-(2,2-di-2-thienyl)-2-hydroxybenzo[b]thiophene-3-carboxamide;

N-[2-phenyl-2-(2-thienyl)ethenyl]-2-hydroxybenzo[b]thiophene-3-carboxamide;

N-[2-(2-furyl)-2-phenylethenyl]-2-hydroxybenzo[b]thiophene-3-carboxamide;

N-methyl-N-(2,2-diphenylethenyl)-2-hydroxybenzo[b]thiophene-3-carboxamide;

N-(2,2-diphenylethenyl)-5-fluoro-2-hydroxybenzo[b]thiophene-3-carboxamide;

N-[2-phenyl-2-(2-thienyl)-ethenyl]-5-cyano-2-hydroxybenzo[b]thiophene-3-carboxamide;

N-[2-phenyl-2-(2-thienyl)-ethenyl]-5-fluoro-2-hydroxy-6-methoxybenzo[b]thiophene-3-carboxamide;

N-[2-phenyl-2-(p-methylthiophenyl)-ethenyl]-2-hydroxy-5-(trifluoromethyl)-benzo[b]thiophene-3-carboxamide;

N-[2-(p-methylthiophenyl)-2-(2-thienyl)-ethenyl]-2-hydroxybenzo[b]thiophene-3-carboxamide;

N-(2,2-diphenylethenyl)-5-(difluoromethyl)-2-hydroxybenzo[b]thiophene-3-carboxamide;

N-[2-phenyl-2-(2-thienyl)-ethenyl]-5-(1,1-difluoroethyl)-2-hydroxybenzo[b]thiophene-3-carboxamide;

N-[2-(3-methyl-2-furyl)-2-phenylethenyl]-5-chloro-2-hydroxybenzo[b]thiophene-3-carboxamide;

N-(2,2-diphenylethenyl)-5-formyl-2-hydroxybenzo[b]thiophene-3-carboxamide;

N-[2-(m-fluorophenyl)-2-phenylethenyl]-2-hydroxy-5-(methylthio)-benzo[b]thiophene-3-carboxamide;

N-[2-(o-fluorophenyl)-2-phenylethenyl]-2-hydroxy-5-(methylthio)-benzo[b]thiophen-3-carboxamide;

N-[2-phenyl-2-(2-thienyl)ethenyl]-2-hydroxy-5-(methylsulfinyl)-benzo[b]thiophene-3-carboxamide.

B. Preparation of the Compounds of the Invention

The compounds of the present invention are prepared from known starting materials via the following method:

N-alkenylation:

An appropriately substituted 2-hydroxybenzo[b]thiophene-3-carboxamide is reacted with an N-alkenylation reagent containing a carbonyl group or the equivalent thereof according to the following scheme:

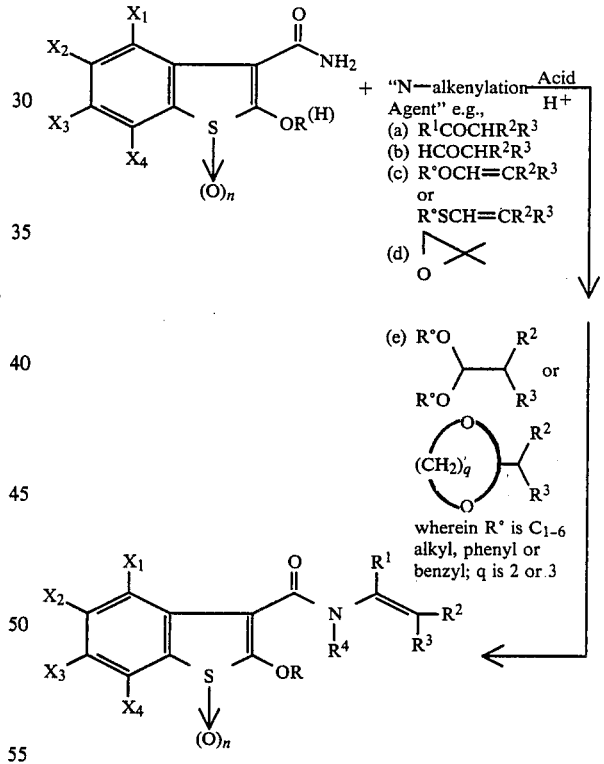

wherein the acid is a strong organic or inorganic acid or a mixture thereof, for example, arylsulfonic acid such as p-toluenesulfonic acid monohydrate, $H_2SO_4$, HCl, $H_3PO_4$, trifluoroacetic acid, alkylsulfonic acid such as methylsulfonic acid, acetic acid, trichloroacetic acid or the like.

The requisite amides, namely substituted 2-hydroxybenzo[b]thiophene-3-carboxamides (I) are prepared via a variety of procedures known to those well versed in the art (See scheme). The following examples are representative but not limiting:

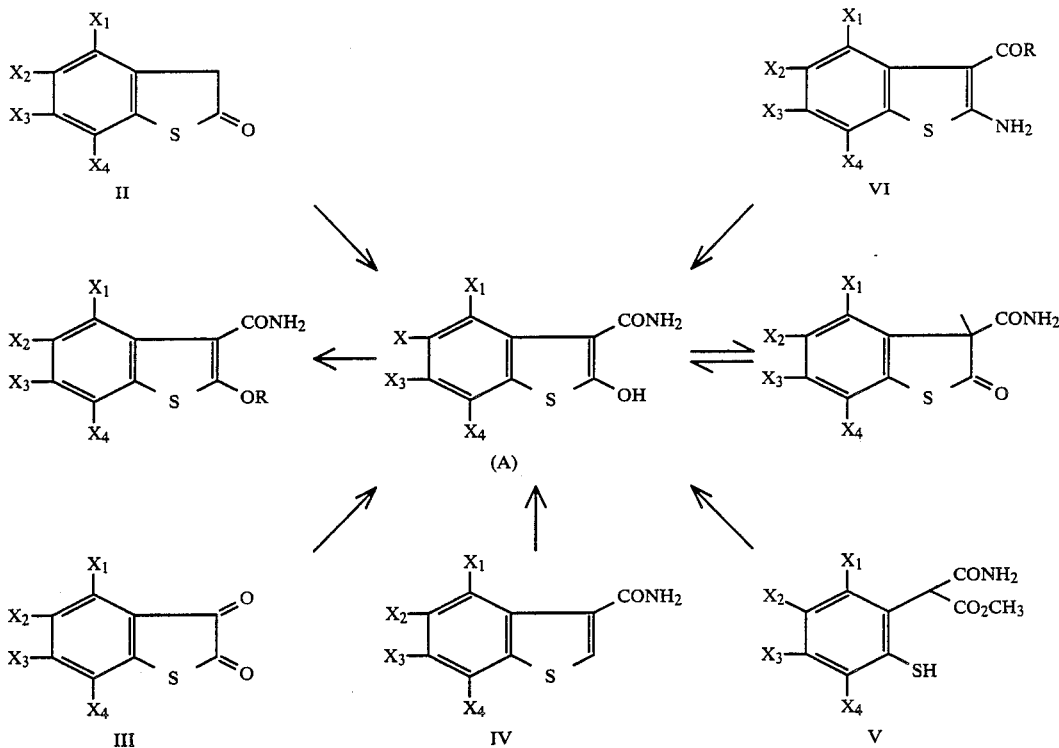

E.g., the known 2-oxobenzothiophene (II) may be converted to 3-carboxamide via several routes, including the reaction with phenyl carbamates (G.B. No. 2,024,220); the conversion of benzothiophen-2,3-dione (III; J. Org. Chem., 727 (1949)) via standard means to the corresponding 3-aldehyde and carboxylic acid, and thence to the amide (A); the conversion of Benzothiophene-3-carboxamides (IV) via oxidation, or other indirect routes to (A); the cyclization of the α-(o-mercaptophenyl)malonamic acids derivatives (V) (G.B. No. 2,024,220) to the corresponding benzothiophene-3-carboxamides; or the transformation of 2-aminobenzthiophenes (VI, Berichte, 101 (1968), 1936) appropriately substituted at the 3-position to the 2-hydroxy compound (A) via diazotization or direct hydrolysis (J. Org. Chem., 30, 4078 (1965)).

Condensation of (A) with the various N-alkylation agents, e.g., those of formula (B) may then be accomplished via procedures previously disclosed in the copending application Ser. No. 705,115 filed Feb. 27, 1985:

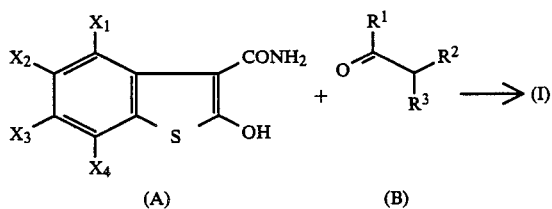

The pharmaceutically acceptable salts of compounds of Formula I (at the 2-hydroxy site when R is H) are readily prepared by conventional procedures well-known in the art. For example, a compound of Formula I is treated with an appropriate amount of a base, such as an alkali or alkaline earth metal hydroxide, e.g. sodium hydroxide, potassium hydroxide, and calcium hydroxide or an organic base such as an alkoxide, e.g., $CH_3ONa$, t-BuOk, or the like.

The pharmaceutically acceptable esters of the phenol of formula (I) can also be prepared by conventional methods. For example, (1) a compound of Formula (I) is treated with an acyl halide such as acetylchloride or an acid anhydride such as acetic acid anhydride.

C. Utility of the compounds within the scope of the invention

This invention also relates to a method of treatment for patients (or mammalian animals raised in the dairy, meat, or fur industries or as pets) suffering from disorders or diseases mediated by prostaglandins and/or leukotrienes, and gastric irritation or lesion. More specifically, this invention is directed to a method of treatment involving the administration of one or more of the dual enzyme inhibitors of formula (I) as the active constituent.

Accordingly, a compound of Formula (I) can be used among other things to reduce pain and inflammation, to correct respiratory, cardiovascular, and intravascular alterations or disorders, and to regulate immediate hypersensitivity reactions that cause human asthma and allergic conditions.

For the treatment of inflammation, arthritis conditions, cardiovascular disorder, allergy, psoriasis, asthma, or other diseases mediated by prostaglandins and/or leukotrienes, a compound of Formula (I) may be administered orally, topically, parenterally, by inhalation spray or rectally in dosage unit formulations containing conventional non-toxic pharmaceutically acceptable carriers, adjuvants and vehicles. The term parenteral as used herein includes subcutaneous injections, intravenous, intramuscular, intravascular injection or infusion techniques. In addition to the treatment of warm-blooded animals such as mice, rats, horses, cattle, sheep, dogs, cats, etc., the compounds of the invention are effective in the treatment of humans.

The pharmaceutical compositions containing the active ingredient may be in a form suitable for oral use, for example, as tablets, troches, lozenges, aqueous or oily suspensions, dispersible powders or granules, emulsions, hard or soft capsules, or syrups or elixirs. Compositions intended for oral use may be prepared according to any method known to the art for the manufacture of pharmaceutical compositions and such compositions may contain one or more agents selected from the group consisting of sweetening agents, flavoring agents, coloring agents and preserving agents in order to provide pharmaceutically elegant and palatable preparations. Tablets contain the active ingredient in admixture with non-toxic pharmaceutically acceptable excipients which are suitable for the manufacture of tablets. These excipients may be for example, inert diluents, such as calcium carbonate, sodium carbonate, lactose, calcium phosphate or sodium phosphate; granulating and disintegrating agents, for example, corn starch, or algenic acid; binding agents, for example starch, gelatin or acacia, and lubricating agents, for example magnesium stearate, stearic acid or talc. The tablets may be uncoated or they may be coated by known techniques to delay disintegration and absorption in the gastrointestinal tract and thereby provide a sustained action over a longer period. For example, a time delay material such as glyceryl monostearate or glyceryl distearate may be employed. They may also be coated by the techniques described in the U.S. Pat. Nos. 4,256,108; 4,166,452; and 4,265,874 to form osmotic therapeutic tablets for control release.

Formulations for oral use may also be presented as hard gelatin capsules wherein the active ingredient is mixed with an inert solid diluent, for example, calcium carbonate, calcium phosphate or kaolin, or as soft gelatin capsules wherein the active ingredient is mixed with water or an oil medium, for example peanut oil, liquid paraffin, or olive oil.

Aqueous suspensions contain the active materials in admixture with excipients suitable for the manufacture of aqueous suspensions. Such excipients are suspending agents, for example sodium carboxymethylcellulose, methylcellulose, hydroxypropylmethylcellulose, sodium alginate, polyvinylpyrrolidone, gum tragacanth and gum acacia; dispersing or wetting agents may be a naturally-occurring phosphatide, for example lecithin or condensation products of an alkylene oxide with fatty acids, for example polyoxyethylene stearate, or condensation products of ethylene oxide with long chain aliphatic alcohols, for example heptadecaethyleneoxycetanol, or condensation products of ethylene oxide with partial esters derived from fatty acids and a hexitol such as polyoxyethylene sorbitol monooleate, or condensation products of ethylene oxide with partial esters derived from fatty acids and hexitol anhydrides, for example polyethylene sorbitan monooleate. The aqueous suspensions may also contain one or more preservatives, for example ethyl, or n-propyl, p-hydroxybenzoate, one or more coloring agents, one or more flavoring agents, and one or more sweetening agents, such as sucrose or saccharin.

Oily suspensions may be formulated by suspending the active ingredient in a vegetable oil, for example arachis oil, olive oil, sesame oil or coconut oil, or in a mineral oil such as liquid paraffin. The oily suspensions may contain a thickening agent, for example beeswax, hard paraffin or cetyl alcohol. Sweetening agents such as those set forth above, and flavoring agents may be added to provide a palatable oral preparation. These compositions may be preserved by the addition of an anti-oxidant such as ascorbic acid. Dispersible powders and granules suitable for preparation of an aqueous suspension by the addition of water provide the active ingredient in admixture with a dispersing or wetting agent, suspending agent and one or more preservatives. Suitable dispersing or wetting agents and suspending agents are exemplified by those already mentioned above. Additional excipients, for example sweetening, flavoring and coloring agents, may also be present.

The pharmaceutical compositions of the invention may also be in the form of oil-in-water emulsions. The oily phase may be a vegetable oil, for example olive oil or arachis oil, or a mineral oil, for example liquid paraffin or mixtures of these. Suitable emulsifying agents may be naturally-occurring gums, for example gum acacia or gum tragacanth, naturally-occurring phosphatides, for example soy bean, lecithin, and esters or partial esters derived from fatty acids and hexitol anhydrides, for example sorbitan monooleate, and condensation products of the said partial esters with ethylene oxide, for example polyoxyethylene sorbitan monooleate. The emulsions may also contain sweetening and flavoring agents.

Syrups and elixirs may be formulated with sweetening agents, for example glycerol, propylene glycol, sorbitol or sucrose. Such formulations may also contain a demulcent, a preservative and flavoring and coloring agents. The pharmaceutical compositions may be in the form of a sterile injectable aqueous or oleagenous suspension. This suspension may be formulated according to the known art using those suitable dispersing or wetting agents and suspending agents which have been mentioned above. The sterile injectable preparation may also be a sterile injectable solution or suspension in a non-toxic parenterally-acceptable diluent or solvent, for example as a solution in 1,3-butane diol. Among the acceptable vehicles and solvents that may be employed are water, Ringer's solution and isotonic sodium chloride solution. In addition, sterile, fixed oils are conventionally employed as a solvent or suspending medium. For this purpose any bland fixed oil may be employed including synthetic mono- or diglycerides. In addition, fatty acids such as oleic acid find use in the preparation of injectables.

The compounds of Formula (I) may also be administered in the form of suppositories for rectal administration of the drug. These compositions can be prepared by mixing the drug with a suitable non-irritating excipient which is solid at ordinary temperatures but liquid at the rectal temperature and will therefore melt in the rectum to release the drug. Such materials are cocoa butter and polyethylene glycols.

For topical use, creams, ointments, jellies, solutions or suspensions, etc., containing the compounds of Formula (I) are employed.

Dosage levels of the order of from about 0.01 mg to about 150 mg per kilogram of body weight per day are useful in the treatment of the above-indicated conditions (about 0.5 mg to about 7.5 gms. per patient per day). For example, inflammation may be effectively treated by the administration of from about 0.2 to 50 mg of the compound per kilogram of body weight per day (about 20 mg to about 3.5 gms per patient per day). Preferably a dosage of from about 1 mg to about 20 mg per kilogram of body weight per day may produce good results (about 25 mg to about 1 gm per patient per day).

The amount of active ingredient that may be combined with the carrier materials to produce a single dosage form will vary depending upon the host treated and the particular mode of administration. For example, a formulation intended for the oral administration of humans may contain from 0.5 mg to 5 gm of active agent compounded with an appropriate and convenient amount of carrier material which may vary from about 5 to about 95 percent of the total composition. Dosage unit forms will generally contain between from about 1 mg to about 500 mg of an active ingredient.

Particularly, for use in treatment of ophthalmic conditions including those associated with elevated intraocular pressure such as glaucoma or other inflammation in the eye. The active compound can be administered topically or systemically when it is appropriate. The dose administered can be from a little as 0.1 to 25 mg or more per day, singly, or preferably on a 2 to 4 dose per day regimen although a single dose per day is satisfactory.

When given systemically, the drug can be given by any route, although the oral route is preferred. In oral administration the drug can be employed in any of the usual dosage forms such as tablets or capsules, either in a contemporaneous delivery or sustained release form. Any number of the usual excipients or tableting aids can likewise be included.

When given by the topical route, the active drug or an ophthalmologically acceptable salt thereof such as the sodium or potassium salt is formulated into an ophthalmic preparation. In such formulations, from 0.1% to 15% by weight can be employed. The objective is to administer a dose of from 0.1 to 10 mg per eye per day to the patient, with treatment continuing so long as the condition persists.

Thus, in an ophthalmic solution, insert, ointment or suspension for topical delivery, or a tablet, intramuscular, or intravenous composition for systemic delivery, the active medicament or an equivalent amount of a salt thereof is employed, the remainder being carrier, excipients, preservatives and the like as are customarily used in such compositions.

The active drugs of this invention are most suitably administered in the form of ophthalmic pharmaceutical compositions adapted for topical administration to the eye such as a suspension, ointment, or as a solid insert. Formulations of these compounds may contain from 0.01 to 15% and especially 0.5% to 2% of medicament. Higher dosages as, for example, about 10%, or lower dosages can be employed provided the dose is effective in reducing or controlling elevated intraocular pressure. As a unit dosage from between 0.001 to 10.0 mg, preferably 0.005 to 2.0 mg, and especially 0.1 to 1.0 mg of the compound is generally applied to the human eye, generally on a daily basis in single or divided doses so long as the condition being treated exists.

As with all medications, dosage requirements are variable and must be individualized on the basis of the disease and the response of the patient.

The pharmaceutical preparation which contains the active compound may be conveniently admixed with a non-toxic pharmaceutical organic carrier, or with a non-toxic pharmaceutical inorganic carrier. Typical of pharmaceutically acceptable carriers are, for example, water, mixtures of water and water-miscible solvents such as lower alkanols or aralkanols, vegetable oils, polyalkylene glycols, petroleum based jelly, ethyl cellulose, ethyl oleate, carboxymethylcellulose, polyvinylpyrrolidone, isopropyl myristate and other conventionally employed acceptable carriers. The pharmaceutical preparation may also contain non-toxic auxiliary substances such as emulsifying, preserving, wetting agents, bodying agents and the like, as for example, polyethylene glycols 200, 300, 400 and 600, carbowaxes 1,000, 1,500, 4,000, 6,000 and 10,000, antibacterial components such as quaternary ammonium compounds, phenylmercuric salts known to have cold sterilizing properties and which are non-injurious in use, thimerosal, methyl and propyl paraben, benzyl alcohol, phenyl ethanol, buffering ingredients such as sodium chloride, sodium borate, sodium acetates, gluconate buffers, and other conventional ingredients such as sorbitan monolaurate, triethanolamine, oleate, polyoxyethylene sorbitan monopalmitylate, dioctyl sodium sulfosuccinate, monothioglycerol, thiosorbitol, ethylenediamine tetraacetic acid, and the like. Additionally, suitable ophthalmic vehicles can be used as carrier media for the present purpose including conventional phosphate buffer vehicle systems, isotonic boric acid vehicles, isotonic sodium chloride vehicles, isotonic sodium borate vehicles and the like.

The pharmaceutical preparation may also be in the form of a solid insert such as one which after dispensing the drug remains essentially intact, or a bio-erodible insert that either is soluble in lacrimal fluids, or otherwise disintegrates.

The following examples of ophthalmic formulations are given by way of illustration.

EXAMPLE 1

| A compound of Formula (I) | 1 mg. | 15 mg. |
| Monobasic sodium phosphate.2H$_2$O | 10 mg. | 5 mg. |
| Dibasic sodium phosphate.12H$_2$O | 30 mg. | 15 mg. |
| Benzalkonium chloride | 0.1 mg. | 0.1 mg. |
| Water for injection q.s. ad. | 1.0 ml. | 1.0 ml. |

Compound A, phosphate buffer salts, and benzalkonium chloride are added to and dissolved in water. The pH of the composition is adjusted to 6.8 and diluted to volume. The composition is rendered sterile by ionizing radiation.

EXAMPLE 2

| A Compound of formula (I) | 5 mg. |
| petrolatum q.s. ad. | 1 gram |

The active compound and the petrolatum are aseptically combined.

EXAMPLE 3

| A Compound of formula (I) | 1 mg. |
| Hydroxypropylcellulose q.s. | 12 mg. |

Ophthalmic inserts are manufactured from compression molded films whichh are prepared on a Carver Press by subjecting the powdered mixture of the above ingredients to a compressional force of 12,000 lbs. (gauge) at 300° F. for one to four minutes. The film is cooled under pressure by having cold water circulate in the platen. Ophthalmic inserts are then individually cut from the film with a rod-shaped punch. Each insert is placed into a vial, which is then placed in a humidity cabinet (88% R.H. at 30° C.) for two to four days. After removal from the humidity cabinet, the vials are stoppered and then capped. The vials containing the hydrate insert are then autoclaved at 250° F. for ½ hour.

EXAMPLE 4

| A Compound of formula (I) | 1 mg. |
|---|---|
| Hydroxypropyl cellulose q.s. ad. | 12 mg. |

Ophthalmic inserts are manufactured from a solvent cast film prepared by making a viscous solution of the powdered ingredients listed above using methanol as the solvent. The solution is placed on a Teflon plate and allowed to dry at ambient conditions. After drying, the film is placed in an 88% R. H. cabinet until it is pliable. Appropriately sized inserts are cut from the film.

EXAMPLE 5

| A Compound of formula (I) | 1 mg. |
|---|---|
| Hydroxypropylmethyl cellulose q.s. ad. | 12 mg. |

Ophthalmic inserts are manufactured from a solvent cast film which is prepared by making a viscous solution of the powdered blend of the above ingredients using a methanol/water solvent system (10 ml. methanol is added to 2.5 g. of the powdered blend, to which 11 ml. of water (in three divided portions) is added. The solution is placed on a Teflon plate and allowed to dry at ambient conditions. After drying, the film is placed in an 88% R. H. cabinet until it is pliable. Appropriately sized inserts are then cut from the film.

EXAMPLE 6

| A Compound of formula (I) | 1 mg. |
|---|---|
| Hydroxypropylmethyl cellulose q.s. ad. | 12 mg. |

Ophthalmic inserts are manufactured from compression molded films which are prepared on a Carver Press by subjecting the powdered mixture of the above ingredients to a compressional force of 12,000 lbs. (gauge) at 350° F. for one minute. The film is cooled under pressure by having cold water circulate in the platen. Ophthalmic inserts are then individually cut from the film with a punch. Each insert is placed into a vial, which is then placed in a humidity cabinet (88% R. H. at 30° C.) for two to four days. After removal from the humidity cabinet, the vials are stoppered and then capped. The vials containing the hydrated insert are then autoclaved at 250° F. for one-half hour.

It is highly preferred that the solid inserts of this invention are available for use by the patient in a pathogen free condition. Thus, it is preferred to sterilize the inserts and to insure against recontamination, the sterilization is preferably conducted after packaging. The best mode of sterilizing is to employ ionizing radiation including radiation emanating from Cobalt 60 or high energy electron beams.

EXAMPLE 7

The following materials are admixed in a 1250 ml bottle: 24 g of an active compound of formula (I) which is a sufficient amount of medicament to result in a concentration of 10 mg per ml in the final samples, allowing for previously established 3.0% average; 0.4 g sodium bisulfite, 12 g NaCl, and 28 ml water (at 180° F.). This mixture, (I), is autoclaved for 30 minutes at 121° C. under 15 psig. Separately, 3 g of hydroxyethylcellulose in 720 ml of water (II) and 0.4 g of lecithin in 80 ml of water (III) were autoclaved for 30 minutes at 121° C. Then, (III) is admixed with (I) for 2 hours, and the resultant mixture poured into (II). Another mixture (IV) is prepared from 20 g of sorbitol, 2.36 ml of benzalkonium chloride, 10 g of disodium edetate, and water to give a final solution volume of 900 ml. Then, (IV) is added to the mixture of (I), (II), and (III) in sufficient quantity to give 1.8 l. overall. The 1.8 l. mixture of I, II, III, and IV is then taken and homogenized using a homogenizer at 2000 psig. Stock solutions are then prepared for polyoxyethylene (20) sorbitan monooleate by dissolving 3 g of the material in 100 ml of water, and of benzyl alcohol/β-phenyl-ethyl alcohol by admixing 50 ml of each alcohol. Varying quantities of the two stock solutions are then added to four 90 ml aliquots of the homogenized mixture of (I), (II), (III), and (IV) prepared as described above, together with sufficient water to give a total of 100 ml for each of four different samples.

Other formulations, in an oil vehicle and an ointment are exemplified in the following examples.

EXAMPLE 8

Solution Composition

| A compound of formula (I) | 0.1 mg. |
|---|---|
| Peanut oil q.s. ad. | 0.10 mg. |

The solution is rendered sterile by filtration through a sterilizing filter.

EXAMPLE 9

| A compound of formula (I) | 0.5 gm. |
|---|---|
| Petrolatum q.s. ad. | 1 gram |

The compound and the petrolatum are aseptically combined.

It will be understood, however, that the specific dose level for any particular patient will depend upon a variety of factors including the activity of the specific compound employed, the age, body weight, general health, sex, diet, time of administration, route of administration, rate of excretion, drug combination and the severity of the particular disease undergoing therapy.

The following examples illustrate the preferred procedures for the synthesis of the compounds of the present invention.

EXAMPLE 10

N-(2,2-Diphenylethenyl)-2-hydroxybenzo(b)thiophene-3-carboxamide

A stirred mixture of 2-hydroxybenzo(b)thiophene-3-carboxamide (0.485 g, 0.0025 m), diphenylacetaldehyde (0.51 g, 0.0026 m), p. toluenesulfonic acid hydrate (30 mg), and dried toluene (15 ml) is set in an oil-bath at 100° C., the bath temperature raised to 150° C., and the mixture heated under reflux until thin-layer chromatography of the mixture indicates completeness of reaction. The cooled reaction mixture is concentrated in vacuo and the residue chromatographed on silica gel (v/v 10–50% CH$_2$Cl$_2$ in hexane) to yield N-(2,2-Diphenylethenyl)-2-hydroxybenzo(b)thiophene-3-carboxamide.

EXAMPLE 11

2-Hydroxybenzo(b)thiophene-3-carboxamide

Method A:

Under a nitrogen atmosphere, a mixture of o-mercaptophenylmalonamic acid (2.1 g, 0.01 m), dimethylformamide (20 ml), and concentrated hydrochloric acid (0.2 ml) are heated in an oil-bath at ca. 100° C. until thin-layer chromatography indicates the absence of starting malonamic acid. The cooled, stirred mixture is diluted with ice-water, aged and filtered to yield 2-hydroxybenzo(b)thiophene-3-carboxamide.

Method B:

Methyl o-mercaptophenylmalonamate (4.5 g, 0.02 m) and dried dimethylformamide (50 ml) at 10° C. is treated with sodium methoxide (3.2 g, 0.06 m) under a nitrogen atmosphere, and the resultant mixture allowed to stir at ambient temperature until no starting malonamate remains (thin-layer analysis). The reaction mixture is added to a stirred excess dilute hydrochloric acid-ice mixture, aged and filtered to yield 2-hydroxybenzo(b)thiophene-3-carboxamide.

When the starting malonamic derivatives of steps A and B are replaced with the corresponding N-benzyl analogs, N-benzyl-2-hydroxybenzo(b)thiophene-3-carboxamide is obtained.

Method C:

A mixture of N-benzyl-2-hydroxybenzo(b)thiophene-3-carboxamide (4.3 g, 0.016 m), 10% palladium on carbon (2.0 g), and ethanol are stirred under a hydrogen atmosphere (40 p.s.i.) at 35° C. until hydrogen uptake is completed. The reaction mixture is filtered, the cake washed well with warm ethanol, and the combined filtrates concentrated in vacuo to yield 2-hydroxybenzo(b)thiophene-3-carboxamide.

Method D:

To a stirred mixture of benzthiophene-2-one (1.50 g, 0.01 m), phenylcarbamate (1.4 g, 0.01 m), and hexamethylphosphorictriamide (2.2 ml) at 5° C. is added sodium hydride (0.24 g, from 0.4 g 60% mineral oil dispersion), and the resultant mixture stirred at ambient temperatures for 5 hours. The volatiles are removed under high vacuum, and the residue triturated well with hexane and then with water to yield 2-hydroxybenzo(b)thiophene-3-carboxamide.

When phenylcarbamate is replaced in the above reaction with N-benzylphenylcarbamate, N-Benzyl-2-hydroxybenzo(b)thiophene-3-carboxamide is obtained.

Method E:

A mixture of 2-acetamido-3-cyanobenzo(b)thiophene (2.2 g, 0.01 m), ethanol (25 ml), water (15 ml) and concentrated hydrochloric acid (25 ml) is heated under reflux for 12 hours. The reaction mixture is diluted with water, aged and filtered to yield 2-hydroxybenzo(b)thiophene-3-carboxamide.

What is claimed is:

1. A compound of formula:

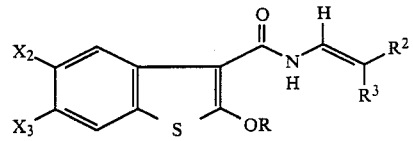

or a pharmaceutically acceptable salt thereof wherein R is
 (a) H;
 (b) C$_{1-6}$alkyl;
 (c) halo C$_{1-6}$alkyl;
X$_2$, X$_3$ independently are
 (a) H;
 (b) C$_{1-6}$alkyl;
 (c) halo C$_{1-6}$alkyl;
 (d) halo;
 (e) cyano;
 (f) methylthio;
 (g) methylsulfonyl; or
 (h) formyl;
R$^2$ and R$^3$ independently are
 (a) phenyl; or
 (b) thienyl.

2. A pharmaceutical composition for treating inflammation, fever and pain in mammalian species comprising a pharmaceutically acceptable carrier and an effective amount of a compound of formula:

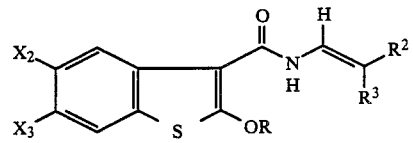

or a pharmaceutically acceptable salt thereof wherein R is
 (a) H;
 (b) C$_{1-6}$alkyl;
 (c) halo C$_{1-6}$alkyl;
X$_2$, X$_3$ independently are
 (a) H;
 (b) C$_{1-6}$alkyl;
 (c) halo C$_{1-6}$alkyl;
 (d) halo;
 (e) cyano;
 (f) methylthio;
 (g) methylsulfonyl; or
 (h) formyl;
R$^2$ and R$^3$ independently are
 (a) phenyl; or
 (b) thienyl.

3. The compound of claim 1 which is N-(2,2-diphenylethenyl)-2-hydroxybenzo[b]thiophene-3-carboxamide.

4. The compound of claim 1 which is N-(2,2-diphenylethenyl)-2-hydroxy-5-(trifluoromethyl)benzo[b]thiophene-3-carbaxamide.

5. The composition of claim 2 which is N-(2,2-diphenylethenyl)-2-hydroxybenzo[b]thiophene-3-carbaxamide.

6. The composition of claim 2 which is N-(2,2-diphenylethenyl)-2-hydroxy-5-(trifluoromethyl)benzo[b]thiophene-3-carbaxamide.

* * * * *